(12) United States Patent
Abraham et al.

(10) Patent No.: US 7,121,999 B2
(45) Date of Patent: Oct. 17, 2006

(54) METHOD OF PREPARING LAYERED GRAFT PROSTHESES

(75) Inventors: Ginger A. Abraham, Braintree, MA (US); James Murray, Whitman, MA (US); Nathaniel M. Bachrach, Brighton, MA (US)

(73) Assignee: Organogenesis Inc., Canton, MA (US)

( * ) Notice: Subject to any disclaimer, the term of this patent is extended or adjusted under 35 U.S.C. 154(b) by 162 days.

(21) Appl. No.: 10/378,483

(22) Filed: Mar. 3, 2003

(65) Prior Publication Data

US 2003/0130747 A1 Jul. 10, 2003

Related U.S. Application Data

(63) Continuation of application No. 09/719,062, filed as application No. PCT/US99/12400 on Jun. 4, 1999, now abandoned.

(60) Provisional application No. 60/120,547, filed on Feb. 17, 1999, provisional application No. 60/088,198, filed on Jun. 5, 1998.

(51) Int. Cl.
*A61F 2/04* (2006.01)
(52) U.S. Cl. .................. 600/36; 623/1.44; 264/496; 424/423
(58) Field of Classification Search ............. 424/423, 424/422, 93.1; 623/1.1, 1.38, 1.44; 600/36; 264/496
See application file for complete search history.

(56) References Cited

U.S. PATENT DOCUMENTS

| | | |
|---|---|---|
| 2,127,903 A | 8/1938 | Bowen |
| 3,272,204 A | 9/1966 | Artandi et al. |
| 3,329,572 A | 7/1967 | Malgouzou |
| 3,551,560 A | 12/1970 | Thiele |
| 3,562,820 A | 2/1971 | Braun |
| 3,914,802 A | 10/1975 | Reick |
| 3,919,411 A | 11/1975 | Glass et al. |
| 3,974,526 A | 8/1976 | Dardik et al. |
| 4,082,507 A | 4/1978 | Sawyer |
| 4,148,664 A | 4/1979 | Cruz, Jr. |
| 4,252,759 A | 2/1981 | Yannas et al. |
| 4,319,363 A | 3/1982 | Ketharanathan |
| 4,323,525 A | 4/1982 | Bornat |
| 4,378,224 A | 3/1983 | Nimni et al. |
| 4,420,339 A | 12/1983 | Kato |
| 4,475,972 A | 10/1984 | Wong |
| 4,502,159 A | 3/1985 | Woodroof et al. |
| 4,539,716 A | 9/1985 | Bell |
| 4,597,762 A | 7/1986 | Walter et al. |
| 4,629,458 A | 12/1986 | Pinchuk |
| 4,703,108 A | 10/1987 | Silver et al. |
| 4,755,593 A | 7/1988 | Lauren |
| 4,787,900 A | 11/1988 | Yannas |
| 4,801,299 A | 1/1989 | Brendel et al. |
| 4,814,120 A | 3/1989 | Huc et al. |
| 4,822,361 A | 4/1989 | Okita et al. |
| 4,842,575 A | 6/1989 | Hoffman, Jr. et al. |
| 4,863,668 A | 9/1989 | Griffiths |
| 4,889,120 A | 12/1989 | Gordon |
| 4,902,289 A | 2/1990 | Yannas |
| 4,902,290 A | 2/1990 | Fleckenstein et al. |
| 4,902,508 A | 2/1990 | Badylak et al. |
| 4,923,380 A | 5/1990 | Huc et al. |
| 4,956,178 A | 9/1990 | Badylak et al. |
| 5,002,583 A | 3/1991 | Pitaru et al. |
| 5,007,934 A | 4/1991 | Stone |
| 5,024,671 A | 6/1991 | Tu et al. |
| 5,026,381 A | 6/1991 | Li |
| 5,028,695 A | 7/1991 | Eckmayer et al. |
| 5,037,377 A | 8/1991 | Alonso |
| 5,061,276 A | 10/1991 | Tu et al. |
| 5,084,065 A | 1/1992 | Weldon et al. |
| 5,106,949 A | 4/1992 | Kemp et al. |
| 5,108,424 A | 4/1992 | Hoffman, Jr. et al. |
| 5,131,908 A | 7/1992 | Dardik et al. |
| 5,192,312 A * | 3/1993 | Orton ................... 600/36 |
| 5,197,977 A | 3/1993 | Hoffman, Jr. et al. |
| 5,219,576 A | 6/1993 | Chu et al. |
| 5,256,418 A | 10/1993 | Kemp et al. |
| 5,263,983 A | 11/1993 | Yoshizato et al. |
| 5,263,984 A | 11/1993 | Li et al. |
| 5,266,480 A | 11/1993 | Naughton et al. |
| 5,281,422 A | 1/1994 | Badylak et al. |
| 5,336,616 A | 8/1994 | Livesey et al. |
| 5,372,821 A | 12/1994 | Badylak et al. |
| 5,374,515 A | 12/1994 | Parenteau et al. |
| 5,376,110 A | 12/1994 | Tu et al. |
| 5,376,376 A | 12/1994 | Li |

(Continued)

FOREIGN PATENT DOCUMENTS

CA 2183056 2/1995

(Continued)

OTHER PUBLICATIONS

Abraham, G., et al., "Evaluation of the Porcine Intestinal Collagen Layer as a Biomaterial", pp. 442-452 (2000).

(Continued)

*Primary Examiner*—Paul B. Prebilic
(74) *Attorney, Agent, or Firm*—Kramer, Levin, Naftalis & Frankel LLP

(57) ABSTRACT

The invention is directed to bioengineered graft prostheses made from two or more superimposed, chemically bonded layers of processed tissue material prepared from cleaned tissue material derived from animal sources. The bioengineered graft prostheses of the invention are prepared using methods that preserve cell compatibility, strength, and bioremodelability of the processed tissue matrix. The bioengineered graft prostheses are used for implantation, repair, or for use in a mammalian host.

4 Claims, No Drawings

U.S. PATENT DOCUMENTS

| | | | |
|---|---|---|---|
| 5,378,469 A | 1/1995 | Kemp et al. | |
| 5,397,353 A | 3/1995 | Oliver et al. | |
| 5,413,597 A | 5/1995 | Krajicek | |
| 5,445,833 A | 8/1995 | Badylak et al. | |
| 5,460,962 A | 10/1995 | Kemp | |
| 5,480,424 A | 1/1996 | Cox | |
| 5,487,895 A | 1/1996 | Dapper et al. | |
| 5,523,291 A | 6/1996 | Janzen et al. | |
| 5,554,389 A | 9/1996 | Badylak et al. | |
| 5,567,806 A | 10/1996 | Abdul-Malak et al. | |
| 5,571,216 A | 11/1996 | Anderson | |
| 5,573,784 A | 11/1996 | Badylak et al. | |
| 5,618,718 A | 4/1997 | Auger et al. | |
| 5,624,840 A | 4/1997 | Naughton et al. | |
| 5,645,860 A | 7/1997 | Knapp, Jr. et al. | |
| 5,667,961 A | 9/1997 | Bernard et al. | |
| 5,693,085 A * | 12/1997 | Buirge et al. | 623/1.13 |
| 5,711,969 A | 1/1998 | Patel et al. | |
| 5,713,950 A | 2/1998 | Cox | |
| 5,716,404 A | 2/1998 | Vacanti et al. | |
| 5,733,337 A | 3/1998 | Carr, Jr. et al. | |
| 5,753,267 A | 5/1998 | Badylak et al. | |
| 5,755,791 A | 5/1998 | Whitson et al. | |
| 5,762,966 A | 6/1998 | Knapp, Jr. et al. | |
| 5,776,182 A | 7/1998 | Bruchman et al. | |
| 5,788,625 A | 8/1998 | Plouhar et al. | |
| 5,800,537 A | 9/1998 | Bell | |
| 5,824,063 A | 10/1998 | Cox | |
| 5,851,230 A | 12/1998 | Weadock et al. | |
| 5,866,414 A | 2/1999 | Badylak et al. | |
| 5,879,383 A | 3/1999 | Bruchman et al. | |
| 5,885,619 A | 3/1999 | Patel et al. | |
| 5,893,888 A | 4/1999 | Bell | |
| 5,922,028 A | 7/1999 | Plouhar et al. | |
| 5,948,654 A | 9/1999 | Tranquillo et al. | |
| 5,955,110 A | 9/1999 | Patel et al. | |
| 5,968,092 A | 10/1999 | Buscemi et al. | |
| 5,968,096 A | 10/1999 | Whitson et al. | |
| 5,993,844 A | 11/1999 | Abraham et al. | |
| 5,997,575 A | 12/1999 | Whitson et al. | |
| 6,090,995 A | 7/2000 | Reich et al. | |
| 6,096,347 A | 8/2000 | Geddes et al. | |
| 6,099,567 A | 8/2000 | Badylak et al. | |
| 6,126,686 A | 10/2000 | Badylak et al. | |
| 6,176,880 B1 | 1/2001 | Plouhar et al. | |
| 6,187,039 B1 | 2/2001 | Hiles et al. | |
| 6,206,931 B1 | 3/2001 | Cook et al. | |
| 6,241,981 B1 | 6/2001 | Cobb et al. | |
| 6,334,872 B1 | 1/2002 | Termin et al. | |
| 6,572,650 B1 | 6/2003 | Abraham et al. | |
| 6,599,690 B1 | 7/2003 | Abraham et al. | |

FOREIGN PATENT DOCUMENTS

| | | |
|---|---|---|
| EP | 0 397 500 A2 | 11/1990 |
| EP | 0 493 788 A1 | 7/1992 |
| EP | 564786 | 10/1993 |
| FR | 2679778 | 3/1991 |
| GB | 2153235 A | 8/1985 |
| JP | S49-28193 | 7/1974 |
| JP | 59-177042 | 10/1984 |
| JP | 60-34450 | 2/1985 |
| JP | 1-230366 | 9/1989 |
| JP | 4-501516 | 3/1992 |
| JP | 5-344988 | 12/1993 |
| WO | WO89/10100 | 11/1989 |
| WO | 93/02666 | 2/1993 |
| WO | 93/10722 | 6/1993 |
| WO | 95/22301 | 8/1995 |
| WO | 95/28183 | 10/1995 |
| WO | 96/31157 | 10/1996 |
| WO | 98/06445 | 2/1998 |
| WO | 98/10775 | 3/1998 |
| WO | 98/25543 | 6/1998 |
| WO | 98/25637 | 6/1998 |
| WO | 98/25964 | 6/1998 |
| WO | WO98/25544 | 6/1998 |
| WO | WO98/25545 | 6/1998 |
| WO | WO98/25546 | 6/1998 |
| WO | WO98/44969 | 10/1998 |
| WO | 98/49969 | 11/1998 |
| WO | 99/12555 | 3/1999 |
| WO | 99/63051 | 12/1999 |
| WO | 00/32250 | 6/2000 |
| WO | 02/22184 | 3/2002 |

OTHER PUBLICATIONS

Angelini G.D., et al., "External Stenting Reduces Early Medial and Neointimal Thickening in a pig Model of Arteriovenous Bypass Grafting", J Thor Cardiovasc Surg., vol. 112, No. 1 (1996).

Badylak, S., et al., "Endothelial Cell Adherence to Small Intestinal Submucosa: An Acellular Bioscaffold", Biomaterials 20, 2257-2263 (1999).

Barra J.A., et al., "Constrictive Perivenous Mesh Prosthesis for Preservation of Vein Integrity", J Thorac. Cardiovasc Surg., 92:330-336 (1986).

Batellier J, et al., "Protection from Atherosclerosis in Vein Grafts by a Rigid External Support", Arteriosel Thromb., 13(3):379-384 (1993).

Bateman J.F. et al., "Induction of Procollagen Processing in Fibroblast Cultures by Neutral Polymers", Journal of Biological Chemistry, 261(9):4198-4203 (1986).

Bodnar, E., et al., "Damage of Porcine Aortic Valve Tissue Caused by the Surfactant Sodiumdodecylsulphate", Thorac. Cardiovascular Surg., 34:82-85 (1986).

Cobb M.A. et al., "Histology After Dural Grafting with Small Intestinal Submucosa", Surg Neurol, 46:389-394 (1996).

Courtman, et al., "Development of a Pericardial Acellular Matrix Biomaterial: Biochemical and Mechanical Effects of Cell Extraction", J. of Biomedical Materials Research, 28:655-666 (1994).

Davis M.G., et al., "Reduction of Experimental Vein Graft Intimal Hyperplasia and Preservation of Nitric Oxide-Mediated Relaxation by the Nitric Oxide Precursos L-arginine", Surgery, 116:557-568 (1994).

Dejardin, L., et al., "Use of Small Intestinal Submucosal Implants for Regeneration of Large Fascial Defects: An experimental Study in Dogs", pp. 203-211 (1999).

Dobrin P.B., et al, "Mechanical Factors Predisposing to Intimal Hyperplasia and Medial Thichening in Autogenous Vein Grafts", Surgery, 105:393-400 (1989).

Egusa, S., "Experimental Study on Vascular Graft II. Replacement of Inferior Vena Cava and Abdoninal Aorta with the Autogenous Segment of Small Intestinal Submucocal", Acta Med. Okayama, 22, 153-165 (1968).

Fillinger MF, et al., "Vein Adaptation to the Hemodynamic Environment of Infrainguinal Grafts", J Vasc Surg., 19(6):970-979 (1994).

Fleischmajer R. et al., "Imunochemistry of a Keratinocyte-Fibroblast Co-culture Model for Model for Reconstruction of Human Skin", J Histochem Cytochem. vol. 41(9):1359-1366 (1993).

Gibbons G.H., et al., "The Emerging Concept of Vascular Remodeling", NEJM, 330(20):1431-1438 (1994).

Gloeckner, D. et al., "Mechanical Evaluation and Design of a Multilayered Collagenous Repair Biomaterial" pp. 365-373 (2000).

Golledge J., et al. "Circumferential Deformation and Shear Stress Induce Differential Responses in Saphenous Vein Endothelium Exposed to Arterial Flow", J. Clin. Invest., 99(11)2719-2726 (1997).

Griffith L.G., et al., "TissueEngineering—Current Challenges and Expanding Opportunities", Science 295:1009-1014 (2002).

Grinnell F., et al., "Collagen Processing, Crosslinking, and Fibril Bundle Assembly in Matrix Produced by Fibroblasts in Long-Term Cultures Supplemented with Ascorbic Acid", Experimental Cell Research, 181:483-491 (1989).

Hata R.I., et al., "L-Ascorbic Acid 2-Phosphate Stimulates Collagen Accumulation, Cell Proliferation, and Formation of a Three-Dimensional Tissuelike Substance by Skin Fibroblasts", Journal of Cellular Physiology, 138:8-16 (1989).

Huynh T.T., et al., "Local Inhibition of Tyrosine Kinase Activity Markedly Attenuates the Development of Intimal Hyperplasia in Experimental Vein Grafts", J Surg Res., 77:104-111 (1998).

Kohler T.R., et al., "The Effect of Rigid External Support on Vein Graft Adaptation to the Arterial Circulation", J Vasc Surg., 9(2):277-285 (1989).

Krippaehne W.W., et al., "Effects of Function on Grafts of Autologous and Homologous Connective Tissue", Surgical Forum, vol. 12, 97-99, 47th Annual Clinical Congress (1961).

Krippaehne W.W., et al., "Studies on the Effect of Stress on Transplants of Autologous and Homologous Connective Tissue", Am. J. Surg., 104:267-272 (1962).

Matsumoto, T. et al., "Further Application of Intestinal Submucosa as a Patch Graft", Surgery, vol. 61(4):584-587 (1967).

Okadome K, et al., "Ultrastructural Evidence of the Effects of Shear Stress Variation on Intimal Thickening in Dogs with Arterially Transplanted Autologous Vein Grafts", J. Cardiovasc Surg., 31:719-726 (1990).

Prevel, C.D., et al. "Experimental Evaluation of Small Intestine Submucosa as a Microvascular Graft Material", Microsurgery, 15:586-591 (1994).

Prevel, C., et al., "Small Intestinal Submucosa: Utilization as a Wound Dressing in Full-Thickness Rodent Wounds", Ann Plast Surg., 35(4):381-388 (1995).

Resnick N., et al., "Hemodynamic Forces are Complex Regulators of Endothelial Gene Expression", FASEB J., 9:874-882 (1995).

Rotthoff, G. et al., "Aortic Replacement with Multi-Layer Submucosa Prostheses made from Heterologous Small Intestine", J. Cardiovas. Surg., 3:31-35.

Steven F.S. et al., "Polymeric Collagen Isolated from the Human Intestinal Submucosa", Gut, 10:484-487 (1969).

Wilson, G.J., et al., "Acellular Matrix: A Biomaterials Approach for Coronary Artery Bypass and Heart Valve Replacement", Ann. Thorac, Surg., 60:S353-S358 (1995).

Yamamura S, et al., "Blood Flow and Kinetics of Smooth Muscle Cell Proliferation in Canine Autogenous Vein Grafts: in Vivo BrdU Incorporation", J Surg Res., 56:155-161 (1994).

Zweep H.P., et al., "Autologous Vein Supported With a Biodegradable Prosthesis for Arterial Grafting", Ann Thorac Surg., 55:427-433 (1993).

Matsumoto et. al., Surgery, 60(3): 739-743 (1966).

Egusa, Acta Med. Okayama 22: 153-165, (1968).

Fraser et al., Arch Surg., 96: 378-385 (1968).

Lawler, Jr. et al., The American Journal of Surgery, 122: 517-519 (1971).

Staros, Biochem., 21: 3950-55 (1982).

Dagan et al., Vascular Surgery, Jul./Aug.: 199-206 (1983).

Broll et al., Eur. Surg. Res. 18: 390-396 (1986).

American National Standard for Vascular Graft Prostheses, Association for the Advancement of Medical Instrumentation, approved Jul. 7, 1986.

Zwolak et al., J. Vasc. Surg., 5: 126-36, (1987).

Haimovici, Vascular Surgery, 3rd Edition: 287-292 (1989).

Silverman, Sterilization and Preservation by Ionizing Irradiation in Disinfection, Sterilization, and Preservation, 4th Edition, Ch. 32: 566-579 (1991).

Schwartz et al., J. Vasc. Surg. 15: 176-186 (1992).

Wyler et al., Journal of Biomedical Materials Research, 26: 1141-1146 (1992).

Abbott et al., Journal of Vascular Surgery, 17 (4): 746-756 (1993).

Hiles et al., Journal of Biomed. Materials Res., 27: 139-144 (1993).

Onohara et al., J. Surg Res., 55: 344-50, (1993).

Carr et al., The Study of the Release of Benzalkonium-Heparin Complex from an Absorbable Synthetic Collagen Graft, The 20th Annual Meeting of the Society for Biomaterials, Apr. 5-9, 1994.

Termin et al., Remodeling of an Absorable Synthetic Collagen Graft: Long Term Implant Histology, The 20th Annual Meeting of the Society for Biomaterials, Apr. 5-9, 1994.

Dobrin, Hypertension, 26: 38-43, (1995).

Kraiss et al., Circ. Res., 79: 45-53, (1996).

Takahashi and Berk, Journal of Clinical Investigation 98: 2623-2631 (1996).

Mehta et al., Nature Medicine, 4: 235-39 (1998).

* cited by examiner

METHOD OF PREPARING LAYERED GRAFT PROSTHESES

This application is a continuation of U.S. application Ser. No. 09/719,062, now abandoned, filed Jun. 11, 2001, which is the National Stage of PCT application No. PCT/US99/12400, filed Jun. 4, 1999, which claims the benefit of and priority to U.S. Provisional Application Ser. No. 60/120,547, filed Feb. 17, 1999 and U.S. Provisional Application Ser. No. 60/088,198, filed Jun. 5, 1998, all of which are hereby incorporated by reference in their entirety.

FIELD OF THE INVENTION

This invention is in the field of tissue engineering. The invention is directed to bioengineered graft prostheses prepared from cleaned tissue material derived from animal sources. The bioengineered graft prostheses of the invention are prepared using methods that preserve cell compatibility, strength, and bioremodelability of the processed tissue matrix. The bioengineered graft prostheses are used for implantation, repair, or for use in a mammalian host.

BRIEF DESCRIPTION OF THE BACKGROUND OF THE INVENTION

The field of tissue engineering combines the methods of engineering with the principles of life science to understand the structural and functional relationships in normal and pathological mammalian tissues. The goal of tissue engineering is the development and ultimate application of biological substitutes to restore, maintain, and improve tissue functions.

Collagen is the principal structural protein in the body and constitutes approximately one-third of the total body protein. It comprises most of the organic matter of the skin, tendons, bones, and teeth and occurs as fibrous inclusions in most other body structures. Some of the properties of collagen are its high tensile strength; its low antigenicity, due in part to masking of potential antigenic determinants by the helical structure; and its low extensibility, semipermeability, and solubility. Furthermore, collagen is a natural substance for cell adhesion. These properties and others make collagen a suitable material for tissue engineering and manufacture of implantable biological substitutes and bioremodelable prostheses.

Methods for obtaining collagenous tissue and tissue structures from explanted mammalian tissues and processes for constructing prosthesis from the tissue, have been widely investigated for surgical repair or for tissue or organ replacement. It is a continuing goal of researchers to develop prostheses that can successfully be used to replace or repair mammalian tissue.

SUMMARY OF THE INVENTION

Biologically-derived collagenous materials such as the intestinal submucosa have been proposed by a many of investigators for use in tissue repair or replacement. Methods for mechanical and chemical processing of the proximal porcine jejunum to generate a single, acellular layer of intestinal collagen (ICL) that can be used to form laminates for bioprosthetic applications are disclosed. The processing removes cells and cellular debris while maintaining the native collagen structure. The resulting sheet of processed tissue matrix is used to manufacture multi-layered laminated constructs with desired specifications. We have investigated the efficacy of laminated patches for soft tissue repair as well as the use of entubated ICL as a vascular graft. This material provides the necessary physical support, while generating minimal adhesions and is able to integrate into the surrounding native tissue and become infiltrated with host cells. In vivo remodeling does not compromise mechanical integrity. Intrinsic and functional properties of the implant, such as the modulus of elasticity, suture retention and UTS are important parameters which can be manipulated for specific requirements by varying the number of ICL layers and the crosslinking conditions.

DETAILED DESCRIPTION OF THE INVENTION

This invention is directed to a tissue engineered prostheses, which, when implanted into a mammalian host, can serve as a functioning repair, augmentation, or replacement body part or tissue structure, and will undergo controlled biodegradation occurring concomitantly with remodeling by the host's cells. The prosthesis of this invention, when used as a replacement tissue, thus has dual properties: First, it functions as a substitute body part, and second, while still functioning as a substitute body part, it functions as a remodeling template for the ingrowth of host cells. In order to do this, the prosthetic material of this invention is a processed tissue matrix developed from mammalian derived collagenous tissue that is able to be bonded to itself or another processed tissue matrix to form a prosthesis for grafting to a patient.

The invention is directed toward methods for making tissue engineered prostheses from cleaned tissue material where the methods do not require adhesives, sutures, or staples to bond the layers together while maintaining the bioremodelability of the prostheses. The terms "processed tissue matrix" and "processed tissue material" mean native, normally cellular tissue that has been procured from an animal source, preferably a mammal, and mechanically cleaned of attendant tissues and chemically cleaned of cells, cellular debris, and rendered substantially free of non-collagenous extracellular matrix components. The processed tissue matrix, while substantially free of non-collagenous components, maintains much of its native matrix structure, strength, and shape. Preferred compositions for preparing the bioengineered grafts of the invention are animal tissues comprising collagen. Collagenous tissue sources including, but not limited to: intestine, fascia lata, pericardium, dura mater, and other flat or planar structured tissues that comprise a collagenous tissue matrix. The structure of these tissue matrices makes them able to be easily cleaned, manipulated, and assembled in a way to prepare the bioengineered grafts of the invention. Other suitable sources with the same flat structure and matrix composition may be identified, procured and processed by the skilled artisan in other animal sources in accordance with the invention.

A more preferred composition for preparing the bioengineered grafts of the invention is an intestinal collagen layer derived from the tunica submucosa of small intestine. Suitable sources for small intestine are mammalian organisms such as human, cow, pig, sheep, dog, goat, or horse while small intestine of pig is the preferred source.

The most preferred composition for preparing the prosthesis of the invention is a processed intestinal collagen layer derived the tunica submucosa of porcine small intestine. To obtain the processed ICL, the small intestine of a pig is harvested and attendant mesenteric tissues are grossly dissected from the intestine. The tunica submucosa is preferably separated, or delaminated, from the other layers of the small intestine by mechanically squeezing the raw intestinal material between opposing rollers to remove the muscular layers (tunica muscularis) and the mucosa (tunica mucosa). The tunica submucosa of the small intestine is harder and stiffer than the surrounding tissue, and the rollers squeeze the softer components from the submucosa. In the examples that follow, the tunica submucosa was mechanically harvested from porcine small intestine using a Bitterling gut cleaning machine and then chemically cleaned to yield a cleaned tissue matrix. This mechanically chemically cleaned intestinal collagen layer is herein referred to as "ICL".

The processed ICL is essentially acellular telopeptide collagen, about 93% by dry weight, with less than about 5% dry weight glycoproteins, glycosaminoglycans, proteoglycans, lipids, non-collagenous proteins and nucleic acids such as DNA and RNA and is substantially free of cells and cellular debris. The processed ICL retains much of its matrix structure and its strength. Importantly, the bioremodelability of the tissue matrix is preserved in part by the cleaning process as it is free of bound detergent residues that would adversely affect the bioremodelability of the collagen. Additionally, the collagen molecules have retained their telopeptide regions as the tissue has not undergone treatment with enzymes during the cleaning process.

The processed tissue layers of the prosthetic device may be from the same collagen material, such as two or more layers of ICL, or from different collagen materials, such as one or more layers of ICL and one or more layers of fascia lata.

The processed tissue matrices may be treated or modified, either physically or chemically, prior to fabrication of a bioengineered graft prosthesis. Physical modifications such as shaping, conditioning by stretching and relaxing, or perforating the cleaned tissue matrices may be performed as well as chemical modifications such as binding growth factors, selected extracellular matrix components, genetic material, and other agents that would affect bioremodeling and repair of the body part being treated, repaired, or replaced.

As ICL is the preferred starting material for the production of the bioengineered graft prostheses of the invention, the methods described below are the preferred methods for producing bioengineered graft prostheses comprising ICL.

In the most preferred embodiment, the tunica submucosa of porcine small intestine is used as a starting material for the bioengineered graft prosthesis of the invention. The small intestine of a pig is harvested, its attendant tissues removed and then mechanically cleaned using a gut cleaning machine which forcibly removes the fat, muscle and mucosal layers from the tunica submucosa using a combination of mechanical action and washing using water. The mechanical action can be described as a series of rollers that compress and strip away the successive layers from the tunica submucosa when the intact intestine is run between them. The tunica submucosa of the small intestine is comparatively harder and stiffer than the surrounding tissue, and the rollers squeeze the softer components from the submucosa. The result of the machine cleaning was such that the submucosal layer of the intestine solely remained.

After mechanical cleaning, a chemical cleaning treatment is employed to remove cell and matrix components, preferably performed under aseptic conditions at room temperature. The intestine is cut lengthwise down the lumen and then cut into sections approximately 15 cm in length. Material is weighed and placed into containers at a ratio of about 100:1 v/v of solution to intestinal material. In the most preferred chemical cleaning treatment, such as the method disclosed in International PCT Application WO 98/49969, the disclosure of which is incorporated herein, the collagenous tissue is contacted with a chelating agent, such as ethylenediaminetetraacetic tetrasodium salt (EDTA) under alkaline conditions, preferably by addition of sodium hydroxide (NaOH); followed by contact with an acid where the acid contains a salt, preferably hydrochloric acid (HCl) containing sodium chloride (NaCl); followed by contact with a buffered salt solution such as 1 M sodium chloride (NaCl)/10 mM phosphate buffered saline (PBS); finally followed by a rinse step using water.

Each treatment step is preferably carried out using a rotating or shaking platform. After rinsing, the ICL is then removed from each container and the ICL is gently compressed of excess water. At this point, the ICL may be stored frozen at −80° C., at 4° C. in sterile phosphate buffer, or dry until use in fabrication of a prosthesis. If stored dry, the ICL sheets are flattened on a surface such as a flat plate, preferably a porous plate or membrane, such as a polycarbonate membrane, and any lymphatic tags from the abluminal side of the material are removed using a scalpel, and the ICL sheets are allowed to dry in a laminar flow hood at ambient room temperature and humidity.

The ICL is a planar sheet structure that can be used to fabricate various types of constructs to be used as a prosthesis with the shape of the prosthesis ultimately depending on its intended use. To form prostheses of the invention, the sheets must be fabricated using a method that preserves the bioremodelability of the processed matrix material but also is able to maintain its strength and structural characteristics for its performance as a replacement tissue. The processed tissue matrix sheets are layered to contact another sheet. The area of contact is a bonding region where layers contact. The bonding region must be able to withstand suturing and stretching while being handled in the clinic, during implantation and during the initial healing phase while functioning as a replacement body part until the patient's cells populate and subsequently bioremodel the prosthesis to form a new tissue.

In a preferred embodiment, the prosthetic device of this invention has two or more superimposed collagen layers that are bonded together. As used herein, "bonded collagen layers" means composed of two or more layers of the same or different collagen material treated in a manner such that the layers are superimposed on each other and are sufficiently held together by self-lamination and chemical linking.

For instance, a multilayer construct of ICL is used to repair body wall structures. It may also be used as, for example, a pericardial patch, a vascular patch, a bladder wall patch, or a hernia repair device or used as a sling to support hypermobile or prolapsed organs. Furthermore, it may also be implanted flat, rolled, or folded for tissue bulking and augmentation. A number of layers of ICL may be incorporated in the construct for bulking or strength indications. Before implantation, the layers may be further treated or coated with collagen or other extracellular matrix components, hyaluronic acid, heparin, growth factors, peptides, or cultured cells.

The preferred embodiment of the invention is directed to flat sheet prostheses, and methods for making and using flat sheet prostheses, comprising of two or more layers of ICL bonded and crosslinked for use as an implantable biomaterial capable of being bioremodeled by a patient's cells. Due to the flat sheet structure of ICL, the prosthesis is easily fabricated to comprise any number of layers, preferably between 2 and 10 layers, more preferably between 2 and 6 layers, with the number of layers depending on the strength and bulk necessary for the final intended use of the construct. The ICL has structural matrix fibers that run in the same general direction. When layered, the layer orientations may be varied to leverage the general tissue fiber orientations in the processed tissue layers. The sheets may be layered so the fiber orientations are in parallel or at different angles. Layers may also be superimposed to form a construct with continuous layers across the area of the prosthesis. Alternatively, as the ultimate size of a superimposed arrangement is limited by the circumference of the intestine, the layers may be staggered, in collage arrangement to form a sheet construct with a surface area larger than the dimensions of the starting material but without continuous layers across the area of the prosthesis. Complex features may be introduced such as a conduit or network of conduit or channels running between the layers or traversing the layers, for example.

In the fabrication of a multilayer construct comprising ICL, an aseptic environment and sterile tools are preferably employed to maintain sterility of the construct when starting with sterile ICL material. To form a multilayer construct of ICL, a first sterile rigid support member, such as a rigid sheet of polycarbonate, was laid down in the sterile field of a laminar flow cabinet. If the ICL sheets are still not in a hydrated state from the mechanical and chemical cleaning processes, they are hydrated in aqueous solution, such as water or phosphate buffered saline. ICL sheets are blotted with sterile absorbent cloths to absorb excess water from the material. If not yet done, the ICL material is trimmed of any lymphatic tags on the serosal surface, from the abluminal side. A first sheet of trimmed ICL is laid on the polycarbonate sheet and is manually smoothed to the polycarbonate sheet to remove any air bubbles, folds, and creases. A second sheet of trimmed ICL is laid on the top of the first sheet, again manually removing any air bubbles, folds, and creases. This is repeated until the desired number of layers for a specific application is obtained, preferably between 2 and 10 layers.

The ICL has a sidedness quality from its native tubular state: an inner mucosal surface that faced the intestinal lumen in the native state and an opposite outer serosal surface that faced the ablumen. It has been found that these surfaces have characteristics that can affect post-operative performance of the prosthesis but can be leveraged for enhanced device performance. Currently with the use of synthetic devices, adhesion formation may necessitate the need for re-operation to release the adhesions from the surrounding tissue. In the formation of a pericardial patch or hernia repair prosthesis having two layers of ICL, it is preferred that the bonding region of the two layers is between the serosal surfaces as the mucosal surfaces have demonstrated to have an ability to resist postoperative adhesion formation after implantation. In other embodiments, it is preferred that one surface of the ICL patch prosthesis be non-adhesive and the other surface have an affinity for adhering to host tissue. In this case, the prosthesis will have one surface mucosal and the other surface serosal. In still another embodiment, it is preferred that the opposing surfaces be able to create adhesions to grow together tissues that contact it on either side, thus the prosthesis will have serosal surfaces on both sides of the construct. Because only the two outer sheets potentially contact other body structures when implanted, the orientation of the internal layers, if the construct is comprised of more than two, is of lesser importance as they will likely not contribute to post-operative adhesion formation.

After layering the desired number of ICL sheets, they are then bonded by dehydrating them together. While not wishing to be bound by theory, dehydration brings the extracellular matrix components, such as collagen fibers, in the layers together when water is removed from between the fibers of the matrix. The layers may be dehydrated either open-faced on the first support member or, between the first support member and a second support member, such as a second sheet of polycarbonate, placed before drying over the top layer of ICL and fastened to the first support member to keep all the layers in flat planar arrangement together with or without a small amount of pressure. To facilitate dehydration, the support member may be porous to allow air and moisture to pass through to the dehydrating layers. The layers may be dried in air, in a vacuum, or by chemical means such as by acetone or an alcohol such as ethyl alcohol or isopropyl alcohol. Dehydration may be done to room humidity, between about 10% Rh to about 20% Rh, or less; or about 10% to about 20% w/w moisture, or less. Dehydration may be easily performed by angling the frame holding the polycarbonate sheet and the ICL layers up to face the oncoming airflow of the laminar flow cabinet for at least about 1 hour up to 24 hours at ambient room temperature, approximately 20° C., and at room humidity.

While it is not necessary, in the preferred embodiment, the dehydrated layers are rehydrated before crosslinking. The dehydrated layers of ICL are peeled off the porous support member together and are rehydrated in an aqueous rehydration agent, preferably water, by transferring them to a container containing aqueous rehydration agent for at least about 10 to about 15 minutes at a temperature between about 4° C. to about 20° C. to rehydrate the layers without separating or delaminating them.

The rehydrated bonded layers are then crosslinked together by contacting the layered ICL with a crosslinking agent, preferably a chemical crosslinking agent that preserves the bioremodelability of the ICL material. As mentioned above, the dehydration brings the extracellular matrix components of adjacent ICL layers together and crosslinking those layers together forms chemical bonds between the components to bond the layers. Crosslinking the bonded prosthetic device also provides strength and durability to the device to improve handling properties. Various types of crosslinking agents are known in the art and can be used such as ribose and other sugars, oxidative agents and dehydrothermal (DHT) methods. A preferred crosslinking agent is 1-ethyl-3-(3-dimethylaminopropyl)carbodiimide hydrochloride (EDC). In an another preferred method, sulfo-N-hydroxysuccinimide is added to the EDC crosslinking agent as described by Staros, J. V., Biochem. 21, 3950–3955, 1982. Besides chemical crosslinking agents, the layers may be bonded together with fibrin-based glues or medical grade adhesives such as polyurethane, vinyl acetate or polyepoxy. In the most preferred method, EDC is solubilized in water at a concentration preferably between about 0.1 mM to about 100 mM, more preferably between about 1.0 mM to about 10 mM, most preferably at about 1.0 mM. Besides water, phosphate buffered saline or (2-[N-morpholino]ethanesulfonic acid) (MES) buffer may be used to dissolve the EDC. Other agents may be added to the solution, such as acetone or an alcohol, up to 99% v/v in water, typically 50%, to make crosslinking more uniform and efficient. These agents remove water from the layers to bring the matrix fibers together to promote crosslinking between those fibers.

The ratio of these agents to water in the crosslinking agent can be used to regulate crosslinking. EDC crosslinking solution is prepared immediately before use as EDC will lose its activity over time. To contact the crosslinking agent to the ICL, the hydrated, bonded ICL layers are transferred to a container such as a shallow pan and the crosslinking agent gently decanted to the pan ensuring that the ICL layers are both covered and free-floating and that no air bubbles are present under or within the layers of ICL constructs. The container is covered and the layers of ICL are allowed to crosslink for between about 4 to about 24 hours, more preferably between 8 to about 16 hours at a temperature between about 4° C. to about 20° C. Crosslinking can be regulated with temperature: At lower temperatures, crosslinking is more effective as the reaction is slowed; at higher temperatures, crosslinking is less effective as the EDC is less stable.

After crosslinking, the crosslinking agent is decanted and disposed of and the constructs are rinsed in the pan by contacting them with a rinse agent to remove residual crosslinking agent. A preferred rinse agent is water or other aqueous solution. Preferably, sufficient rinsing is achieved by contacting the chemically bonded construct three times with equal volumes of sterile water for about five minutes for each rinse. Using a scalpel and ruler, constructs are trimmed to the desired size; a usable size is about 6 inches square (approx. 15.2 cm×15.2 cm) but any size may be prepared and used for grafting to a patient.

Constructs are then terminally sterilized using means known in the art of medical device sterilization. A preferred method for sterilization is by contacting the constructs with sterile 0.1% peracetic acid (PA) neutralized with a sufficient amount of 10 N sodium hydroxide (NaOH), according to U.S. Pat. No. 5,460,962, the disclosure of which is incorporated herein. Decontamination is performed in a container on a shaker platform, such as 1 L Nalge containers, for about 18±2 hours. Constructs are then rinsed by contacting them with three volumes of sterile water for 10 minutes each rinse.

Another preferred sterilization means is by gamma irradiation. Constructs are packaged in bags made from material suitable for gamma irradiation and sealed using a vacuum sealer, which in turn are placed in hermetic bags for gamma irradiation between 25.0 and 35.0 kGy. Gamma irradiation significantly, but not detrimentally, decreases Young's modulus, ultimate tensile strength, and shrink temperature. The mechanical properties after gamma irradiation are still sufficient for use in a range of applications and gamma irradiation is a preferred means for sterilizing as it is widely used in the field of implantable medical devices.

In still another preferred embodiment, after ICL is reformed into a construct for tissue repair or replacement, it may be populated with cells to form a cellular tissue construct comprising bonded layers of ICL and cultured cells. Cellular tissue constructs can be formed to mimic the organs they are to repair or replace.

Cell cultures are established from mammalian tissue sources by dissociating the tissue or by explant method. Primary cultures are established and cryopreserved in master cell banks from which portions of the bank are thawed, seeded, and subcultured to expand cell numbers. To populate an acellular ICL construct with cells, the construct is placed in a culture dish or flask and contacted by immersion in media containing suspended cells. Because collagen is a natural substance for cell adhesion, cells bind to the ICL construct and proliferate on and into the collagenous matrix of the construct.

Preferred cell types for use in this invention are derived from mesenchyme. More preferred cell types are fibroblasts, stromal cells, and other supporting connective tissue cells, or human dermal fibroblasts. Human fibroblast cell strains can be derived from a number of sources, including, but not limited to neonate male foreskin, dermis, tendon, lung, umbilical cords, cartilage, urethra, corneal stroma, oral mucosa, and intestine. The human cells may include but need not be limited to: fibroblasts, smooth muscle cells, chondrocytes and other connective tissue cells of mesenchymal origin. It is preferred, but not required, that the origin of the matrix-producing cell used in the production of a tissue construct be derived from a tissue type that it is to resemble or mimic after employing the culturing methods of the invention. For instance, a multilayer sheet construct is cultured with fibroblasts to form a living connective tissue construct; or myoblasts, for a skeletal muscle construct. More than one cell type can be used to populate an ICL construct, for example, a tubular ICL construct can be first cultured with smooth muscle cells and then the lumen of the construct populated with the first cell type is cultured with vascular endothelial cells as a second cell type to form a cellular vascular replacement device. Similarly, a urinary bladder wall patch prosthesis is prepared on multilayer ICL sheet constructs using smooth muscle cells as a first cell type and then urinary endothelial cells as a second cell type. Cell donors may vary in development and age. Cells may be derived from donor tissues of embryos, neonates, or older individuals including adults. Embryonic progenitor cells such as mesenchymal stem cells may be used in the invention and induced to differentiate to develop into the desired tissue.

Although human cells are preferred for use in the invention, the cells to be used in the method of the are not limited to cells from human sources. Cells from other mammalian species including, but not limited to, equine, canine, porcine, bovine, ovine, and murine sources may be used. In addition, cells that are genetically engineered by spontaneous, chemical, or viral transfection may also be used in this invention. For those embodiments that incorporate more than one cell type, mixtures of normal and genetically modified or transfected cells may be used and mixtures of cells of two or more species or tissue sources may be used, or both.

Recombinant or genetically-engineered cells may be used in the production of the cell-matrix construct to create a tissue construct that acts as a drug delivery graft for a patient needing increased levels of natural cell products or treatment with a therapeutic. The cells may produce and deliver to the patient via the graft recombinant cell products, growth factors, hormones, peptides or proteins for a continuous amount of time or as needed when biologically, chemically, or thermally signaled due to the conditions present in the patient. Cells may also be genetically engineered to express proteins or different types of extracellular matrix components which are either 'normal' but expressed at high levels or modified in some way to make a graft device comprising extracellular matrix and living cells that is therapeutically advantageous for improved wound healing, or facilitated or directed neovascularization. These procedures are generally known in the art, and are described in Sambrook et al, *Molecular Cloning, A Laboratory Manual*, Cold Spring Harbor Press, Cold Spring Harbor, N.Y. (1989), incorporated herein by reference. All of the above-mentioned types of cells may be used in this invention for the production of a cellular tissue construct formed from an acellular construct formed from bonded ICL layers.

The prostheses of this invention, functioning as a substitute body part, may be flat, tubular, or of complex geometry. The shape of the formed prosthesis will be decided by its intended use. Thus, when forming the bonding layers of the prosthesis of this invention, the mold or plate support member can be fashioned to accommodate the desired shape. The flat multilayer prostheses can be implanted to repair, augment, or replace diseased or damaged organs, such as abdominal wall, pericardium, hernias, and various other organs and structures including, but not limited to, bone, periosteum, perichondrium, intervertebral disc, articular cartilage, dermis, bowel, ligaments, and tendons. In addition, the flat multilayer prostheses can be used as a vascular or intra-cardiac patch, or as a replacement heart valve.

Flat sheets may also be used for organ support, for example, to support prolapsed or hypermobile organs by using the sheet as a sling for the organs, such as bladder or uterus. Tubular prostheses may be used, for example, to replace cross sections of tubular organs such as vasculature, esophagus, trachea, intestine, and fallopian tubes. These organs have a basic tubular shape with an outer surface and an inner luminal surface. In addition, flat sheets and tubular structures can be formed together to form a complex structure to replace or augment cardiac or venous valves.

The bioengineered graft prostheses of the invention may be used to repair or replace body structures that have been damaged or diseased in host tissue. While functioning as a substitute body part or support, the prosthesis also functions as a bioremodelable matrix scaffold for the ingrowth of host cells. "Bioremodeling" is used herein to mean the production of structural collagen, vascularization, and cell repopulation by the ingrowth of host cells at a rate about equal to the rate of biodegradation, reforming and replacement of the matrix components of the implanted prosthesis by host cells and enzymes. The graft prosthesis retains its structural characteristics while it is remodeled by the host into all, or substantially all, host tissue, and as such, is functional as an analog of the tissue it repairs or replaces.

Young's Modulus (MPa) is defined as the linear proportional constant between stress and strain. The Ultimate Tensile Strength (N/mm) is a measurement of the strength across the prosthesis. Both of these properties are a function of the number of layers of ICL in the prosthesis. When used as a load bearing or support device, it should be able to withstand the rigors of physical activity during the initial healing phase and throughout remodeling.

Lamination strength of the bonding regions is measured using a peel test. Immediately following surgical implantation, it is important that the layers not delaminate under physical stresses. In animal studies, no explanted materials showed any evidence of delamination. Before implantation, the adhesion strength between two opposing layers is about 8.1±2.1 N/mm for a 1 mM EDC crosslinked multilayer construct.

Shrink Temperature (° C.) is an indicator of the extent of matrix crosslinking. The higher the shrink temperature, the more crosslinked the material. Non-crosslinked, gamma-irradiated ICL has a shrink temperature of about 60.5±1.0. In the preferred embodiment, an EDC crosslinked prostheses will preferably have a shrink temperature between about 64.0±0.2° C. to about 72.5±1.1° C. for devices that are crosslinked in 1 mM EDC to about 100 mM EDC in 50% acetone, respectively.

The mechanical properties include mechanical integrity such that the prosthesis resists creep during bioremodeling, and additionally is pliable and suturable. The term "pliable" means good handling properties for ease in use in the clinic.

The term "suturable" means that the mechanical properties of the layer include suture retention which permits needles and suture materials to pass through the prosthesis material at the time of suturing of the prosthesis to sections of native tissue. During suturing, such prostheses must not tear as a result of the tensile forces applied to them by the suture, nor should they tear when the suture is knotted. Suturability of the prostheses, i.e., the ability of prostheses to resist tearing while being sutured, is related to the intrinsic mechanical strength of the prosthesis material, the thickness of the graft, the tension applied to the suture, and the rate at which the knot is pulled closed. Suture retention for a highly crosslinked flat 6 layer prosthesis crosslinked in 100 mM EDC and 50% acetone is about 6.7±1.6 N. Suture retention for a 2 layer prosthesis crosslinked in 1 mM EDC in water is about 3.7 N±0.5 N. The preferred lower suture retention strength is about 2N for a crosslinked flat 2 layer prosthesis as a surgeon's force in suturing is about 1.8 N.

As used herein, the term "non-creeping" means that the biomechanical properties of the prosthesis impart durability so that the prosthesis is not stretched, distended, or expanded beyond normal limits after implantation. As is described below, total stretch of the implanted prosthesis of this invention is within acceptable limits. The prosthesis of this invention acquires a resistance to stretching as a function of post-implantation cellular bioremodeling by replacement of structural collagen by host cells at a faster rate than the loss of mechanical strength of the implanted materials due from biodegradation and remodeling.

The processed tissue material of the present invention is "semi-permeable," even though it has been layered and bonded. Semi-permeability permits the ingrowth of host cells for remodeling or for deposition of agents and components that would affect bioremodelability, cell ingrowth, adhesion prevention or promotion, or blood flow. The "non-porous" quality of the prosthesis prevents the passage of fluids intended to be retained by the implantation of the prosthesis. Conversely, pores may be formed in the prosthesis if a porous or perforated quality is required for an application of the prosthesis.

The mechanical integrity of the prosthesis of this invention is also in its ability to be draped or folded, as well as the ability to cut or trim the prosthesis obtaining a clean edge without delaminating or fraying the edges of the construct.

The following examples are provided to better explain the practice of the present invention and should not be interpreted in any way to limit the scope of the present invention. It will be appreciated that the device design in its composition, shape, and thickness is to be selected depending on the ultimate indication for the construct. Those skilled in the art will recognize that various modifications can be made to the methods described herein while not departing from the spirit and scope of the present invention.

EXAMPLES

Example 1

Chemical Cleaning of Mechanically Cleaned Porcine Small Intestine

The small intestine of a pig was harvested and mechanically stripped, using a Bitterling gut cleaning machine (Nottingham, UK) which forcibly removes the fat, muscle and mucosal layers from the tunica submucosa using a combination of mechanical action and washing using water. The mechanical action can be described as a series of rollers that compress and strip away the successive layers from the tunica submucosa when the intact intestine is run between them. The tunica submucosa of the small intestine is comparatively harder and stiffer than the surrounding tissue, and the rollers squeeze the softer components from the submucosa. The result of the machine cleaning was such that the submucosal layer of the intestine solely remained.

The remainder of the procedure, chemical cleaning according to International PCT Application No. WO 98/49969 to Abraham, et al., was performed under aseptic conditions and at room temperature. The chemical solutions were all used at room temperature. The intestine was then cut lengthwise down the lumen and then cut into 15 cm sections. Material was weighed and placed into containers at a ratio of about 100:1 v/v of solution to intestinal material.

A. To each container containing intestine was added approximately 1 L solution of 0.22 μm (micron) filter sterilized 100 mM ethylenediaminetetraacetic tetrasodium salt (EDTA)/10 mM sodium hydroxide (NaOH) solution. Containers were then placed on a shaker table for about 18 hours at about 200 rpm. After shaking, the EDTA/NaOH solution was removed from each bottle.

B. To each container was then added approximately 1 L solution of 0.22 μm filter sterilized 1 M hydrochloric acid (HCl)/1 M sodium chloride (NaCl) solution. Containers were then placed on a shaker table for between about 6 to 8 hours at about 200 rpm. After shaking, the HCl/NaCl solution was removed from each container.

C. To each container was then added approximately 1 L solution of 0.22 μm filter sterilized 1 M sodium chloride (NaCl)/10 mM phosphate buffered saline (PBS). Containers were then placed on a shaker table for approximately 18 hours at 200 rpm. After shaking, the NaCl/PBS solution was removed from each container.

D. To each container was then added approximately 1 L solution of 0.22 μm filter sterilized 10 mM PBS. Containers were then placed on a shaker table for about two hours at 200 rpm. After shaking, the phosphate buffered saline was then removed from each container.

E. Finally, to each container was then added approximately 1 L of 0.22 μm filter sterilized water. Containers were then placed on a shaker table for about one hour at 200 rpm. After shaking, the water was then removed from each container.

Processed ICL samples were cut and fixed for histological analyses. Hemotoxylin and eosin (H&E) and Masson's trichrome staining was performed on both cross-section and long-section samples of both control and treated tissues. Processed ICL tissue samples appeared free of cells and cellular debris while untreated control samples appeared normally and expectedly very cellular.

Example 2

Comparative Study of Other Cleaning Treatments for Collagenous Tissue

Other methods for disinfecting and sterilizing collagenous tissues described in U.S. Pat. No. 5,460,962 to Kemp were compared to similar methods described by Cook, et al. in International PCT application WO 98/22158. Examples 1, 2, and 3, from Kemp, in addition to a non-buffered peracetic acid method were done.

Small intestines were harvested from 4 large pigs. Intestines were procured, the outer mesenteric layer was stripped, and the intestines were flushed with water.

The study included seven conditions: Condition A was carried out according to the disclosure of Example 1 in Cook, et al. in International PCT Application WO 98/22158. Condition B was a variation of A in that the intestinal material was mechanically cleaned before employing the disclosed chemical treatment. Conditions C, D, and E were carried out according to the methods of Examples 1, 2, and 3 in U.S. Pat. No. 5,460,962 to Kemp. In all conditions, a ten-to-one ratio of solution to material is used, that is, 100 g of tissue material is treated with 1 L of solution.

A. Material from each of the 4 intestines were placed into separate bottles (n=5) containing a one liter solution of 0.2% peracetic acid in 5% ethanol (pH 2.56) and agitated on a shaker platform. After two hours of agitation, condition A was mechanically cleaned on the Bitterling gut cleaning machine.

For the other six conditions, B through G, intestine was mechanically cleaned using the Bitterling gut cleaning machine prior to chemical treatment. After mechanical cleaning, representative pieces from the 4 intestines were placed into bottles containing solution for chemical treatment. Bottles were shaken 18±2 hours on a platform. The remaining six conditions, B through G, were as follows:

B. A one liter solution of 0.2% peracetic acid in 5% ethanol (pH 2.56) (n=5).

C. A one liter solution of 0.1% peracetic acid in phosphate buffered saline (pH 7.2) (n=3).

D. A one liter solution of 0.1% peracetic acid and 1M sodium chloride (NaCl) (pH 7.2) (n=3).

E. A one liter solution of 0.1% peracetic acid and 1M NaCl (pH 2.9) (n=3).

F. One liter solution of "chemical cleaning" solutions as mentioned above in Example 1 (n=4).

G. A one liter solution of 0.1% peracetic acid in deionized water, buffered to pH 7.0 (n=2).

After chemical and mechanical treatments, all conditions were rinsed for a total of 4 times with filtered sterile purified water. The mechanically and chemically treated material was grossly stained to examine cellular debris with Mayer's hematoxylin. Morphological assessment included Hematoxylin & Eosin, Masson's Trichrome, and Alizarin Red staining techniques. Histological results from the various treatments show that the method of condition A yielded a material where it was difficult to remove mucosal layers on Bitterling after chemical treatment. The material had to be run through Bitterling about an extra 10–12 times. The material was very swollen at first and had a significantly large amount of cellular debris on surface and in the vasculature of the material. The method of condition B was also very swollen and also demonstrated a significantly large amount of cellular debris on surface and in the vasculature of the material. The methods of conditions C and D yielded a non-swollen material having minimal cellular debris in vasculature. Condition E yielded a material that was slightly swollen and contained minimal cellular debris in the vasculature.

A DNA/RNA isolation kit (Amersham Life Sciences) was used to quantify the residual DNA/RNA contained in the cleaned tissues. The results are summarized in Table 1.

TABLE 1

| DNA/RNA Isolation kit Results (μg DNA/mg tissue) | | | | | | | |
|---|---|---|---|---|---|---|---|
| Condition | A | B | C | D | E | F | G |
| Average ± Std. Dev. | 2.16 ± 0.32 | 2.1 ± 0.48 | 0.32 ± 0.11 | 1.92 ± 0.28 | 0.32 ± 0.23 | 0 ± 0 | 1.42 ± 0.03 |

Morphological analysis correlates with the DNA/RNA quantification to show that the cleaning regimens of conditions A and B result in a collagenous tissue matrix that remains highly cellular and contain residual DNA as a result. The cleaning methods of Kemp are much more effective for the removal of cells and cellular debris from collagenous tissue matrices. Finally, the chemical cleaning method of Condition F, described in International PCT Application No. WO 98/49969 to Abraham, et al. and outlined in Example 1, above, removes all cells and cellular debris and their DNA/RNA to a level undetectable by these methods.

Example 3

Method for Fabricating a Multilayer ICL Construct

ICL processed according to the method of Example 1 was used to form a multilayer construct having 2 layers of ICL. A sterile sheet of porous polycarbonate (pore size, manufacturer) was laid down in the sterile field of a laminar flow cabinet. ICL was blotted with sterile TEXWIPES (LYM-TECH Scientific, Chicopee, Mass.) to absorb excess water from the material. ICL material was trimmed of its lymphatic tags from the abluminal side and then into pieces about 6 inches in length (approx. 15.2 cm). A first sheet of trimmed ICL was laid on the polycarbonate sheet, mucosal side down, manually removing any air bubbles, folds, and creases. A second sheet of trimmed ICL was laid on the top facing, or abluminal side, of the first sheet with the abluminal side of the second sheet contacting the abluminal side of the first sheet, again manually removing any air bubbles, folds, and creases. The polycarbonate sheet with the ICL layers was angled up with the ICL layers facing the oncoming airflow of the laminar flow cabinet. The layers were allowed to dry for about 18±2 hours in the cabinet at room temperature, approximately 20° C. The dried layers of ICL were then peeled off the polycarbonate sheet together without separating or delaminating them and were transferred to a room temperature waterbath for about 15 minutes to hydrate the layers.

Chemical crosslinking solution of 100 mM EDC/50% Acetone was prepared immediately before crosslinking as EDC will lose its activity over time. The hydrated layers were then transferred to a shallow pan and the crosslinking agent gently decanted to the pan ensuring that the layers were both covered and free-floating and that no air bubbles were present under or within the constructs. The pan was covered and allowed to sit for about 18±2 hours in fume hood. The crosslinking solution was decanted and disposed. Constructs were rinsed in the pan three times with sterile water for about five minutes for each rinse. Using a scalpel and ruler, constructs were trimmed to the desired size.

Constructs were decontaminated with sterile 0.1% peracetic acid (PA) treatment neutralized with sodium hydroxide $_{10}$N NaOH according to U.S. Pat. No. 5,460,962,the disclosure of which is incorporated herein. Constructs were decontaminated in 1 L Nalge containers on a shaker platform for about 18±2 hours. Constructs were then rinsed with three volumes of sterile water for 10 minutes each rinse and PA activity was monitored by Minncare strip testing to ensure its removal from the constructs.

Constructs were then packaged in plastic bags using a vacuum sealer which were in turn placed in hermetic bags for gamma irradiation between 25.0 and 35.0 kGy.

Example 4

Implant Studies Using Multilayer ICL Constructs

New Zealand white rabbits were used for in vivo analysis and all procedures were performed in compliance with Animal Care and Use Committee (ACUC) guidelines. A full thickness defect of approximately two inches was created through the rectus abdominis muscle in each animal and then was repaired with a 6 layer patch prosthesis. Patches were removed at 30, 66, 99 and 180 days post-implant. Three rabbits were sacrificed at each time point and examined for any evidence of herniation, swelling, infection or adhesions. Explanted patches were fixed in formalin and stained with hematoxylin and eosin or alizarin red for histologic evaluation of cell infiltration, inflammatory response and calcification. In some cases, unfixed patches were evaluated to determine the effect of implantation on the mechanical characteristics using uniaxial MTS analysis.

All animals underwent an uneventful post-operative course with no swelling, herniation or inflammation at the repair site of the abdominal wall. At the time of the explant, the inner surface of the patch was covered with a glistening tissue layer that appeared to be continuous with the parietal peritoneum. In one animal explanted after 30 days, a grade one adhesion to the explanted abdominal viscera was seen and appeared to be associated with the suture line rather than the implant itself. Neovascularization of the peritoneal surface of the patches was observed at all time points.

Within 30 days, the peritoneal surface of the patch was covered with mesothelium. Inflammatory cells typical of a foreign body response were present throughout the explant but more prevalent at the periphery of the patch. The inflammatory cells consisted mostly of macrophages and multinucleated giant cells with fewer lymphocytes, heterophils and fibroblasts. After implantation for 66 days, the histology was similar but with fewer inflammatory cells. In addition, the patches had begun to incorporate into the native abdominal wall tissue. At 99 and 180 days, infiltration of host fibroblasts was apparent by hematoxylin and eosin staining and by Masson trichrome staining. Alizarin red staining for calcium showed that there was no evidence of calcification in the patch material. Small focal areas of calcification were associated with the suture material.

Mechanical Testing was performed at the time of explant to determine the ultimate tensile strength (UTS) of the construct. Briefly, the tissue was excised leaving approximately 1 inch of surrounding tissue from the edges of the construct. The surrounding tissue at opposite ends of the construct was then gripped and pulled to failure in uniaxial tension at a constant strain rate of $0.013$ s$^{-1}$ using a servohydraullic MTS testing system with TestStar-SX software. The UTS was then calculated from the peak force. All failures occurred within the tissue region of the testing specimens, suggesting that the construct was equal to or stronger than surrounding tissue, was well integrated into surrounding tissue, and maintained sufficient strength in its performance as a hernia repair patch.

The combination of mechanical properties and potential for good integration into the host tissue make the ICL a promising material for soft tissue repair. These studies have shown that the formation of adhesions is minimal and there is no indication of calcification in the patches. Preliminary analysis of the mechanical characteristics suggests that this collagen construct can maintain the necessary strength while remodeling and incorporating into the surrounding tissue. This ability of the patch to remodel provides an advantage over prosthetic materials that do not integrate well into the surrounding tissue.

Example 5

Mechanical Testing Techniques and Properties of Multilayer ICL Prostheses

Preferred embodiments of multilayer ICL patch constructs formed by the method of Example 3, including gamma irradiation were tested. Constructs of 2, 4, and 6 layers of ICL crosslinked with 100 mM EDC in 50% Acetone (100/50) and 6 layer constructs with crosslinked with 7 mM EDC/90% acetone v/v in water (7/90) and 1 mM EDC in water (1/0) were evaluated along a number of measures. Results are summarized in Table 2.

Tensile failure testing was performed using a servohydraullic MTS testing system with TestStar-SX software. Strips 1.25 cm in width were pulled to failure in uniaxial tension at a constant strain rate of $0.013$ s$^{-1}$. The slope of the linear region ($E_Y$) and the ultimate tensile strength (UTS) were calculated from the stress strain curves.

The adhesion strength between the layers was tested using a standard protocol for the testing of adhesives (ASTM D1876-95). The adhesion strength is the average force required to peel apart two layers of laminated ICL at a constant velocity of 0.5 cm/sec.

A differential scanning calorimeter was used to measure the heat flow to and from a sample under thermally controlled conditions. The shrink temperature was defined as the onset temperature of the denaturation peak in the temperature-energy plot. Suture retention was not performed on 2 or 4 layer constructs cross-linked in 100 mM EDC and 50% acetone since the suture retention (3.7N±0.5 N) for a 2 layer construct cross-linked in 1 mM EDC and no acetone (much less cross-linked) was well above the 2 N minimum specification. Lamination strength between ICL layers and shrinkage temperature are dependent on the crosslinking concentration and the addition of acetone rather than the number of layers in a construct.

TABLE 2

Mechanical Properties of Multilayer ICL Constructs

| Mechanical Analysis | 2 Layer 100/50 | 4 Layer 100/50 | 6 Layer 100/50 | 6 Layer 7/90 | 6 Layer 1/0 |
|---|---|---|---|---|---|
| Ultimate Tensile Strength (N/mm) | 0.6 ± 0.1 | 3.1 ± 0.2 | 2.0 ± 0.2 | 2.7 ± 0.2 | 1.3 ± 0.4 |
| Young's Modulus (MPa) | 38.0 ± 5.8 | 49.5 ± 4.0 | 35.9 ± 2.6 | 43.0 ± 1.2 | 14.5 ± 7.8 |
| Lamination Strength (N/m) | 39.7 ± 6.1 | | | 63.1 ± 24.4 | 8.1 ± 2.1 |
| Suture Retention (N) | not tested | no tested | 6.6 ± 1.6 | 10.6 ± 2.2 | 10.9 ± 2.8 |
| Shrink Temperature (° C.) | 72.5 ± 1.1 | | | 69.5 ± 0.1 | 64.0 ± 0.2 |

Although the foregoing invention has been described in some detail by way of illustration and example for purposes of clarity and understanding, it will be obvious to one of skill in the art that certain changes and modifications may be practiced within the scope of the appended claims.

We claim:
1. The method of preparing a prosthesis having two or more superimposed, bonded layers of processed tissue matrix, comprising:
   (a) layering two or more sheets of hydrated processed tissue matrix;
   (b) dehydrating said layers to adhere the layers together;
   (c) crosslinking said layers with a crosslinking agent to bond the layers together; and,
   (d) rinsing said layers to remove the crosslinking agent; wherein said thus formed prosthesis when implanted into a mammalian patient, undergoes controlled biodegradation occurring with adequate living cell replacement such that the original implanted prosthesis is remodeled by the patient's living cells,
wherein the processed tissue matrix is prepared by;
   (e) mechanically cleaning the layers of tissue matrix and
   (f) chemically cleaning the layers of tissue matrix,
wherein chemically cleaning the layers of tissue matrix comprises:
   (g) contacting the tissue matrix with a chelating agent under alkaline conditions;
   (h) contacting the tissue matrix with an acid containing a salt;
   (i) contacting the tissue matrix with a buffered salt solution; and
   (j) rinsing the tissue matrix.
2. The method of claim 1, wherein the chelating agent comprises ethylenediaminetetracetic acid.
3. The method of claim 1, wherein the acid containing a salt comprises hydrochloric acid containing sodium chloride.
4. The method of claim 1, wherein the buffered salt solution comprises sodium chloride in phosphate buffered saline.

* * * * *